United States Patent
Gagnieu et al.

(10) Patent No.: US 10,004,825 B2
(45) Date of Patent: Jun. 26, 2018

(54) COLLAGEN MATERIALS AND METHODS FOR OBTAINING SAME

(71) Applicant: BIOM'UP, Saint-Priest (FR)

(72) Inventors: Christian Gagnieu, Chassieu (FR); Patricia Forest, Lyons (FR); Sylvain Picot, Lyons (FR)

(73) Assignee: BIOM'UP, Saint-Priest (FR)

( * ) Notice: Subject to any disclaimer, the term of this patent is extended or adjusted under 35 U.S.C. 154(b) by 233 days.

(21) Appl. No.: 14/860,363

(22) Filed: Sep. 21, 2015

(65) Prior Publication Data

US 2016/0008509 A1 Jan. 14, 2016

Related U.S. Application Data

(62) Division of application No. 13/266,370, filed as application No. PCT/EP2010/055681 on Apr. 28, 2010, now Pat. No. 9,168,326.

(30) Foreign Application Priority Data

Apr. 28, 2009 (FR) ...................... 09 52768

(51) Int. Cl.
| | | |
|---|---|---|
| A61L 27/24 | (2006.01) | |
| A61L 27/58 | (2006.01) | |
| A61F 2/00 | (2006.01) | |
| A61F 2/08 | (2006.01) | |
| C07K 14/78 | (2006.01) | |

(52) U.S. Cl.
CPC ............ *A61L 27/24* (2013.01); *A61F 2/0077* (2013.01); *A61F 2/08* (2013.01); *A61L 27/58* (2013.01); *C07K 14/78* (2013.01); *A61L 2430/10* (2013.01); *Y10T 428/1348* (2015.01); *Y10T 442/20* (2015.04)

(58) Field of Classification Search
None
See application file for complete search history.

(56) References Cited

U.S. PATENT DOCUMENTS

| | | | |
|---|---|---|---|
| 4,931,546 A | | 6/1990 | Tardy et al. |
| 5,157,111 A | * | 10/1992 | Pachence ................ A61L 27/34 128/DIG. 8 |
| 6,451,032 B1 | * | 9/2002 | Ory ........................ A61L 31/10 424/445 |
| 2003/0040113 A1 | | 2/2003 | Mizuno et al. |
| 2006/0099268 A1 | | 5/2006 | Chan et al. |
| 2007/0260299 A1 | | 11/2007 | Gagnieu |
| 2009/0054984 A1 | | 2/2009 | Shortkroff et al. |

FOREIGN PATENT DOCUMENTS

| | | |
|---|---|---|
| EP | 0731163 A2 | 9/1996 |
| EP | 0862468 | 9/1998 |
| EP | 1797124 A1 | 6/2007 |
| FR | 2724563 A1 | 3/1996 |
| FR | 2810889 A1 | 1/2002 |
| FR | 2877669 A1 | 5/2006 |
| FR | 2902661 A1 | 12/2007 |
| JP | 6-292716 A | 10/1994 |
| JP | 8-243156 A | 9/1996 |
| JP | 11-319068 A | 11/1999 |
| JP | 2006-87596 A | 4/2006 |
| JP | 2007-503852 A | 3/2007 |
| JP | 2008-515848 A | 5/2008 |
| WO | WO 98/15299 | 4/1998 |
| WO | WO 2005/018491 A2 | 3/2005 |
| WO | WO 2006/037770 A1 | 4/2006 |
| WO | WO 2007/147739 A2 | 12/2007 |

OTHER PUBLICATIONS

Besseau et al., "Stabilization of Fluid Cholesteric Phases of Collagen to Ordered Gelated Matrices", J. Mol. Biol., vol. 251 (1995) pp. 197-202.
Chan et al., "Photochemical crosslinking improves the physicochemical properties of collagen scaffolds", J. Biomed. Mater. Res., 75A (2005) pp. 689-701.
Ehrmann RL et al. "The Growth of Cells on a Transparent Gel of Reconstituted Rat-Tail Collagen", Journal of the National Cancer Institute, V. 16, No. 6, 1956, pp. 1375-1403.
Forest et al., "Influence of gradual introduction of hydrophobic groups (stearic acid) in denatured atelocollagen on fibroblasts behavior in vitro", J. Biomed. Mater Res 80A, (2006) pp. 758-767.
French Office Action issued in French Patent Application No. 0952768 dated Dec. 2, 2009.
Gagnieu et al., "In vivo biodegradability and biocompatibility of porcine type I atelocollagen newly crosslinked by oxidixed glycogen", Bio-Medical Materials and Engineering, vol. 17 (2007) pp. 9-18.
International Search Report issued in PCT/EP2010/055681 dated Jun. 22, 2010.
Japanese Office Action for corresponding Japanese Application No. 2012-507724 dated Apr. 4, 2014 (with English translation).
Kakade et al., "Determination of Available Lysine in Proteins", Analytical Biochemistry, vol. 27 (1696) pp. 273-280.
Rousseau et al., "In vitro cytocompatibility of porcine type I atelocollagen crosslinked by oxidized glycogen", Biomaterials, vol. 23 (2002) pp. 1503-1510.

* cited by examiner

*Primary Examiner* — Paul J Holland
(74) *Attorney, Agent, or Firm* — Birch, Stewart, Kolasch & Birch, LLP

(57) ABSTRACT

The invention relates to novel collagen materials and, specifically, collagen membranes, tubes and threads. Said materials combine enhanced properties of resilience and strength. The invention also relates to a method for preparing collagen materials using acid fibrous collagen comprising coagulation and, optionally, cross-linking of the collagen in the presence of ammonia gas.

13 Claims, No Drawings

COLLAGEN MATERIALS AND METHODS FOR OBTAINING SAME

CROSS REFERENCE TO RELATED APPLICATIONS

This application is a Divisional of application Ser. No. 13/266,370 (issued as U.S. Pat. No. 9,168,326), filed on Oct. 26, 2011, which was filed as the national phase under 35 U.S.C. § 371 of PCT International Application No. PCT/EP2010/055681 on Apr. 28, 2010, which claims priority to patent application Ser. No. 0,952,768, filed in France on Apr. 28, 2009, all of which are hereby expressly incorporated by reference into the present application.

The invention relates to novel collagen materials and, more particularly, to collagen membranes, tubes, films, sponges, gels, matrices and threads. Said materials combine excellent properties of elasticity and mechanical strength. The invention also relates to a method for preparing collagen materials using acidic fibrous collagen of tendons which further comprises controlled cross-linking of the collagen. The invention also relates to acidic fibrous collagen of tendons with long fibers, to a method for obtaining same as well as the application of same in the manufacture notably of collagen membranes, tubes, films, sponges, gels, matrices and threads.

Collagen is a protein known since antiquity. For many years it has been used for the manufacture of medical devices because of its remarkable physicochemical and biological properties. Historically used to prepare hemostatic compresses, its biocompatibility and its activity on wound healing and scarring make it a material of choice for preparing biomaterials such as membranes for guided tissue regeneration in dental surgery and for coating materials used in parietal reinforcements and vascular prostheses, in order to facilitate their integration and to guarantee their tightness.

Materials made entirely of collagen, such as hemostatic compresses, membranes to prevent adhesion and conduits for nerve regeneration (WO2007/147739, FR2810889), are available commercially.

Provided that the collagen extraction process leads to sufficient purification, said products are perfectly biocompatible and fulfill their functions well.

Depending on the indications and thus the desired duration of resorption in the body, collagen may be cross-linked. Methods for cross-linking collagen are well known and widely described. Mention may be made, for example, of EP0862468 and U.S. Pat. No. 4,931,546. The use of oxidized glycogen as a collagen cross-linking agent has already been described in FR2877669 as well as in the publications by Forest et al. and Rousseau et al. According to the nature and the proportion of the cross-linking agent, as well as to the cross-linking conditions (pH, reaction time), it is relatively easy to vary in a controlled manner the resorption time of a material. However, the difficulty in cross-linking lies notably in the choice of cross-linking rate, which must make it possible to produce a stable and reproducible material that has the desired resorption time and has defined mechanical properties compatible with the application. This problem is all the more important for long-lifespan materials because the more a collagen material is cross-linked the more rigid it is. This physical characteristic, expressed as an increase in susceptibility to tearing and a decrease in suture retention strength, may be totally unacceptable for certain surgical uses. However, there is at present no cross-linking method that precisely and reproducibly controls collagen cross-linking rate, and thus controls the rigidity of the final material.

Thus, in certain cases, and notably when the materials are subjected to strong mechanical stresses by the surgeon and/or by the patient after the implantation, said existing collagen materials reach their limits. Such is the case, for example, for the material described in the patent FR2877669 and in the scientific publication by Forest et al. (2007). Said materials fulfill their functions very well, but in extreme cases where the sutures are delicate or the stresses greater, the material is not sufficiently strong.

The mechanical properties of a collagen material depend on three factors:
- the choice of the level of structuring of the collagen,
- the choice of the reticulating agent and the cross-linking rate,
- the methods for preparing and forming the material.

Surgeons, faced with new surgical techniques and a wide range of possibilities, have an ever-increasing interest in biodegradable products that are strong enough to be sutured and placed under tension, optionally though not necessarily reinforced by a textile lattice, for example. This is notably the case for membranes for guided tissue regeneration. To prepare such a material, the person skilled in the art will choose a highly structured collagen and will strongly cross-link the collagen. However, the result will be a product that is very rigid, breakable and difficult for the surgeon to handle. The selected collagen may be so-called fibrous collagen, i.e., not very unstructured, but a lack of control in the extraction process limits the possibilities of materials produced with said collagens. Cross-linking will be carried out either by immersion or by contacting with formaldehyde or glutaraldehyde vapor, for example, but without producing flexible and controlled cross-linking. Thus, there are today no collagen materials that are mechanically strong (tension, suture) while being flexible and conformable and that have a suitable resorption time (several months).

The manufacture of cross-linked collagen materials generally includes preparing an aqueous collagen solution, optionally adding a cross-linking agent, forming the material by casting or molding the collagen solution, evaporating the solvent and then treating the material obtained by physical or chemical processes, in baths, vapors or under reduced pressure in order to form cross-linking bonds, removing and/or deactivating the residual cross-linking agent or any undesired molecule, and then a new step of drying the material if the final form of the material requires such a step.

Said methods of the state of the art require numerous manipulations of the collagen material and do not enable satisfactory control of the cross-linking step, in particular in terms of cross-linking bond density and collagen structure. Notably, said methods do not enable a coagulation/fibrillation step or a coagulation/fibrillation/cross-linking step that is sufficiently progressive to enable three-dimensional organization of the collagen molecules. As a result, the cross-linked materials generally obtained are either strong and rigid or flexible but relatively weak.

The present invention will now described a method for obtaining a collagen material and, notably, collagen membranes that have high tensile strength and tear strength, while preserving sufficient flexibility and elasticity for surgical applications in particular.

Indeed, the Inventors have developed a novel method for preparing collagen material comprised of treating wet fibrous collagen with ammonia gas during the forming of the collagen material. Said progressive treatment with ammonia gas makes it possible to obtain both coagulation and fibrillation of fibrous collagen during its forming. The invention thus also relates to a method for forming fibrous collagen and notably to the use of a weak base such as ammonia gas to ensure the complete coagulation and fibrillation of collagen in gel form. Said method also enables the concomitant cross-linking of collagen during its forming by directly adding cross-linking agent to the fibrous collagen solution before forming by casting or molding. The collagen cross-linking rate may thus be controlled in a precise and reproducible manner.

Furthermore, the method may enable appreciably homogeneous cross-linking in the material, i.e., the cross-linking rate may be virtually identical on the outside and on the inside of the material. This notably enables said material to have improved properties compared to materials whose cross-linking is much greater on the outside than on the inside, or even non-existent on the inside.

The method may thus provide a material with improved mechanical and/or resorption properties. Without wanting to be bound by this theory, it is possible that resorption rate is better controlled by virtue of the cross-linking and/or structural homogeneity in the volume of material. Notably in the context of the present invention, "better controlled" means that from one sample of the material to the next, in particular from two different manufacturing batches, and/or from one patient to the next, the resorption rate exhibits differences that are smaller than in the case of materials resulting from known methods of the prior art.

Furthermore, the material may have a resorption that is appreciably constant, or linear, as a function of time. This may thus lead to progressive release of the degraded portions.

On the other hand, in the case of existing materials in which cross-linking is not homogeneous throughout the volume, degradation may be sudden. Without wanting to be bound by this theory, it is probable that once the external portion is degraded, the internal portion, with a lower degree of cross-linking, is degraded much more rapidly, or even very rapidly. This may thus cause a rapid increase in the quantity of degradation products, which may cause inflammatory reactions, or even a sudden inflammatory flare-up.

Preferentially, said methods are implemented with fibrous collagen and preferably with collagen with long fibers. The Inventors have also developed a method for preparing acidic fibrous collagen of tendons that have the characteristic of particularly long and elastic fibers. The fibrous collagen obtained may be used to prepare collagen materials, notably the membranes, films, sponges, gels, matrices, threads and tubes according to the invention.

The methods according to the present invention make it possible to manufacture medical devices and, notably, membranes, films, sponges, gels, matrices, threads and tubes with properties in terms of mechanical strength, elasticity, suturability and conformability never achieved with standard collagen material production methods. The materials obtained by the methods according to the invention may be used in general and specialized surgery, notably for urologic, gynecologic, cardiac, thoracic, vascular, articular, digestive, plastic, spinal, neurological, orthopedic, trauma, dental, oral and maxillofacial surgeries, for guided cicatrization or tissue substitution (dura mater, gums, bones, nerves, tendons, ligaments, viscera, pericardium, peritoneum, conjunctive tissues in general, dermis, muscle, cartilage), regardless of the form the material thus manufactured may take.

Said materials, considering their characteristics, may be used in membrane or film form as a guided cicatrization and/or an anti-adhesion barrier in any surgery in which the separation of two organs or tissues is necessary during the cicatrization phases, such as a regeneration guide in tube or sleeve form fabricated by the surgeon to his or her liking in nerve and tendon regeneration, or a regeneration matrix for tissue engineering when the collagen is in sponge form, for example. The conformability of the materials, due to the collagen used for their manufacture, makes them easy to use and enables them to follow the contours of the tissues on which they are placed while being suturable in order to be maintained in place if need be. Depending on the implantation site and the desired resorption time, cross-linking may be adjusted by varying the proportion of reactive groups of the cross-linking agent and those of the collagen in the starting collagen solution (and/or by increasing or decreasing ammonia quantity and/or ammonia contact time). The thickness of the material may also be adjusted to the same ends.

Preferred applications are the obtaining of membranes (for guided tissue regeneration and tissue substitution (dura mater, pericardium, etc.) in many types of surgery), tubes (for nerve regeneration, for example for tendon and ligament regeneration) and matrices (for example for tissue engineering).

SUMMARY OF THE INVENTION

The invention relates to a method for preparing acidic fibrous collagen of tendons comprising the following steps:
 a) swelling tendons of pig, calf, lamb, foal or mixtures thereof in 0.1 M to 0.5 M aqueous acetic acid solution for at least 7 days,
 b) mechanically grinding the tendons to obtain an aqueous suspension,
 c) precipitating and washing fibrous collagen from the aqueous suspension of step b),
 d) dehydrating the collagen,
 e) obtaining acidic fibrous collagen.

Preferably, step a) involves swelling tendons of pigs younger than 10 months.

Preferentially, in step c) the collagen is precipitated and washed in 0.45-1.2 M NaCl solution.

Typically, in step d) the dehydrating of the collagen comprises treatment with acetone.

The invention also relates to acidic fibrous collagen of tendons that may be obtained by the method according to the invention. Advantageously, the invention relates to fibrous collagen that has long fibers such that in a 0.1% aqueous solution less than 20%, 15% or 10% of the fibers contained in the solution are retained on a 50 μm nylon filter and more than 20%, 25% or 30% cross a 5 μm nylon filter.

The invention also relates to a method for preparing a collagen material comprising the following steps:
 a) preparing an aqueous solution of collagen in acid form,
 b) optionally, adding an aldehyde cross-linking agent that is non-reactive at acidic pH,
 c) molding or casting the aqueous collagen solution,
 d) coagulating, and optionally cross-linking, the aqueous collagen solution by treating with ammonia gas,
 e) removing excess ammonia and obtaining the collagen material by drying.

Preferably, the aqueous solution of step a) comprises 0.05% to 3% by weight of collagen in acid form.

Preferentially, the collagen in acid form is native collagen or denatured collagen.

Preferentially, the aqueous solution of step a) is prepared with acidic fibrous collagen selected from collagens of pig tendons, calf tendons, lamb tendons and foal tendons.

In an advantageous embodiment, coagulating and optionally cross-linking the collagen solution are carried out by treating with ammonia gas for at least 24 hours.

In an advantageous embodiment, the method comprises adding an aldehyde cross-linking agent that is non-reactive at acidic pH and coagulating and cross-linking the aqueous collagen solution by treating with ammonia gas.

Advantageously, the aldehyde cross-linking agent is selected from glycogen and aldehyde amylopectins.

More advantageously, the aldehyde cross-linking agent is oxidized glycogen.

Preferentially, the aldehyde cross-linking agent is added in proportions ranging from 0.05 to 5 for the CHO ratio of the aldehyde cross-linking agent on the $NH_2$ of the collagen.

In a preferred embodiment of the method according to the invention, the collagen material is a membrane, in step c) the aqueous collagen solution is deposited on a flat mold and in step e) excess ammonia is removed and a collagen membrane is obtained by drying.

The invention also relates to collagen material that may be obtained by a method according to the invention and/or as described in the present description. More particularly, said material is obtained by said method; indeed said material is directly obtained by said method.

According to another of its aspects, the invention also relates to a collagen material, notably a membrane, with homogeneous cross-linking.

In the context of the present invention, "homogeneous cross-linking" means that the difference between the cross-linking on the outside surface and the cross-linking on the inside, notably toward, indeed in, the middle of the material is less than or equal to 25%, notably less than or equal to 20%, in particular less than or equal to 15%, indeed less than or equal to 10%, and quite particularly less than or equal to 5%.

The cross-linking difference in percentage may correspond to the absolute value of [((external cross-linking−internal cross-linking)/(internal cross-linking+external cross-linking))×100].

Cross-linking may be evaluated by the number of moles of free lysine per mg of material, notably in the manner described in example 7.

The material, notably the membrane, with homogeneous cross-linking may have a dry thickness of at least 50 µm, and quite particularly its length, its width and its height are each greater than or equal to 50 µm.

Quite particularly, the material is in the form of a membrane with a dry thickness of at least 50 µm. The length and the width of said membrane may be greater than or equal to 1 cm, indeed 5 cm.

According to still another of its aspects, the invention relates to a collagen material that has an increase in denaturation temperature greater than or equal to 3° C., notably greater than or equal to 5° C., indeed greater than or equal to 7° C., in relation to non-cross-linked collagen material. This difference in cross-linking temperature may be measured by differential scanning calorimetry (DSC), notably in the manner described in example 8.

The cross-linked collagen material may have an increase in denaturation temperature in relation to non-cross-linked material of at least 5%, in particular 8%, notably at least 10%.

This percentage of increase in temperature corresponds to the following equation: [((cross-linked material denaturation temperature/non-cross-linked material temperature)−1)× 100].

The increase in the denaturation temperature of the cross-linked material in relation to the denaturation temperature of non-cross-linked material may be used to verify that said material is actually cross-linked.

Preferably, said collagen material may consist of a collagen membrane, a collagen film, a collagen thread, a collagen tube, a collagen sponge or a collagen gel.

In a preferred embodiment, the invention relates to a collagen membrane that may be obtained by the method according to the invention and that has a dry thickness between 30 µm and 200 µm, preferentially between 80 µm and 120 µm.

Preferably, the collagen membrane consists of a non-porous collagen monolayer with a dry thickness between 50 µm and 150 µm, preferentially between 80 µm and 120 µm.

The collagen membrane obtained according to the invention advantageously has a density between 12 $mg/cm^2$ and 16 $mg/cm^2$, a swelling ratio less than 6, a suture retention strength greater than 1 N, a yield strength greater than 4 MPa and a percentage of enzymatic degradation by trypsin less than 35%.

The invention also relates to a collagen membrane that has a dry thickness between 80 µm and 120 µm, a density between 12 $mg/cm^2$ and 16 $mg/cm^2$, a swelling ratio less than 6, a suture retention strength greater than 1 N, a yield strength greater than 4 MPa and a percentage of enzymatic degradation by trypsin less than 35%.

More preferentially, the invention relates to a collagen membrane that has a swelling ratio between 4 and 6, a suture retention strength between 1 N and 2.5 N, a yield strength between 4 Mpa and 7 MPa and a percentage of enzymatic degradation by trypsin between 20% and 35%.

Advantageously, the collagen membrane obtained is reinforced with a resorbable or non-resorbable textile.

DETAILED DESCRIPTION OF THE INVENTION

The invention thus relates to a method for extracting collagen from tendons of young animals leading to a collagen whose fiber length and elasticity, during its use in the manufacture of medical devices, make it possible to obtain materials that are mechanically strong, elastic, suturable and conformable.

Thus, one object of the invention relates to a method for preparing acidic fibrous collagen of tendons comprising the following steps:
  a) swelling tendons of pig, calf, lamb, foal or mixtures thereof in 0.1 M to 0.5 M aqueous acetic acid solution for at least 7 days,
  b) mechanically grinding the tendons to obtain an aqueous suspension,
  c) precipitating and washing the fibrous collagen from the aqueous suspension of step b),
  d) dehydrating the collagen.

Preferably, the extracting of fibrous collagen is carried out from tendons of animals younger than 10 months, and more preferentially from tendons of pigs younger than 10 months.

The first step thus comprises harvesting tendons from the feet of pigs younger than 10 months (tendons may also be harvested from calves, lambs and foals), cleaning, thoroughly removing conjunctive tissues and other non-tendinous tissues and then cutting the tendons into approximately 1 cm-long pieces and rinsing them with water.

Swelling is carried out for at least 7 days and up to 15 days, preferentially 15 days, in a 0.1 M to 0.5 M, preferentially 0.3 M, acetic acid bath under stirring in a ratio of 1 kg of tendons in a volume between 20 l and 30 l, preferentially 25 l.

The second step consists of gentle grinding, enabling the release of long tendon fibers from the swollen tendon fragments. The grinding of a volume of swelling bath containing pieces of swollen tendons is carried out for example for 2 min at 3000 rpm and then a series of steps, each comprising dilution of the medium with water followed by grinding under the same conditions, are carried out until a paste with a dry matter concentration between 4.8 g/kg and 6.5 g/kg is obtained.

The third step consists of precipitating fibrous collagen from the paste that resulted from the grinding, and then purifying it according to standard methods. This step may comprise one or more precipitations using sodium chloride at a final concentration between 0.45 M and 1.2 M, more particularly at a concentration of 0.6 M, and one or more steps of washing the precipitated collagen in a 0.45 M to 1.2 M, preferentially 0.6 M, NaCl solution. In general, the method also comprises a step of viral inactivation in 1 N sodium hydroxide solution at 20° C. for 1 hour. By its hydrolytic action on non-collagenous proteins, this step constitutes additional purification. At the end of this step, new washes with 0.6 M NaCl are carried out. In order to dehydrate the collagen and to remove salts, acetone treatment is then carried out and a dry fiber is thus obtained.

This particular method applied to tendons leads to collagen that is different from existing collagens in that it is composed of long fibers without containing pieces of tissues and it preserves a portion of soluble collagen.

The invention thus also relates to acidic fibrous collagen of tendons that may be obtained by the methods according to the invention.

The invention also relates to fibrous collagen such that in 0.1% aqueous solution less than 20%, 15% or 10% of the fibers contained in the solution are retained on a 50 µm nylon filter and more than 20%, 25% or 30% cross a 5 µm nylon filter.

The protocol for measuring fractions of fibrous collagen obtained according to the invention, of less than 5 µm and greater than 50 µm in size, is as follows:

Prepare 0.1% aqueous collagen solution under magnetic or mechanical stirring for 16 to 24 hours (500 mg used).

Deposit the solution on a 5 µm or 50 µm nylon mesh mounted on a 9 cm-diameter circular support. The molecules diffuse in the mesh at atmospheric pressure. The pressure exerted on the mesh is considered negligible as the height of the water column does not exceed 4 cm for a 63 cm$^2$ section.

The solution on the mesh is stirred with a flat square blade that does not scrape across the fabric but is positioned a few millimeters (at most 5) above the fabric. Stirring speed is 80 rpm.

The width of the blade is 7 cm. It is positioned in the center of the circular support.

After the collagen solution stops flowing through the mesh, the retentate is washed with 50 ml of 0.05 M acetic acid while observing pressure differentials until the flow stops. This operation is repeated three times.

The fractions are then recovered (filtrate and retentate) and the collagen is precipitated from each fraction by adding NaCl in order to achieve a final concentration of 0.6 M.

The precipitate is then collected by centrifugation or filtration and then dehydrated with acetone, dried under reduced pressure and weighed.

The invention also relates to methods for forming acidic collagen for preparing a collagen material.

In a first embodiment, the invention relates to a method for preparing a collagen material characterized in that it comprises the following steps:
a) preparing an aqueous solution comprising 0.05% to 3% by weight of collagen in acid form,
b) molding or casting the aqueous collagen solution,
c) coagulating the aqueous collagen solution by treating with ammonia gas,
d) removing the ammonia and obtaining the collagen material.

In a particularly advantageous embodiment, the invention thus relates to a method for preparing a collagen material characterized in that it comprises the following steps:
a) preparing an aqueous solution of collagen in acid form,
b) adding an aldehyde cross-linking agent that is non-reactive at acidic pH,
c) molding or casting the aqueous collagen solution,
d) coagulating and cross-linking the aqueous collagen solution by treating with ammonia gas,
e) removing the ammonia and obtaining the collagen material.

The first step of the methods according to the invention consists of preparing an aqueous collagen solution. "Aqueous collagen solution" also refers to a collagen suspension.

The method according to the invention uses collagen in acid form. "Collagen in acid form" refers to collagen in which most of the carboxylic functional groups are protonated and which has an acidic pH in solution or suspension in water.

Preferably, the method for preparing the collagen material according to the invention uses acidic fibrous collagen.

"Fibrous collagen" refers to collagen in which the molecules of collagen are not individualized or are poorly individualized, and which is thus composed of fibers and fibrils made up of collagen molecules naturally linked together by weak and covalent bonds, and by aggregates of such structures. Fibrous collagen, notably, consists of large particles (mainly greater than 5 µm when hydrated) which give a homogeneous suspension by dispersion in aqueous medium.

Fibrous collagen may notably be fibrous collagen of skin or fibrous collagen of tendons. Fibrous collagen of skin comprises relatively short fibers due to the natural organization of the tissue, acid-soluble collagen and small aggregates. Collagen of tendons comprises long fibers and very little soluble collagen.

Preferably, the methods according to the present invention are implemented with fibrous collagen of tendons, preferably with fibrous collagen of pig tendons and more preferentially with collagen of tendons of pigs younger than 10 months.

Advantageously, the methods of the present invention use acidic fibrous collagen of tendons prepared according to the method described above and with long fibers.

The first step thus consists of dissolving the collagen in water. It is carried out according to standard methods described in the literature. When the collagen is an acidic fibrous collagen, this step enables the suspension of fibers surrounded by microfibrillar collagen and so-called soluble collagen that have maintained a structure necessary to fibrillation.

Typically, the aqueous collagen solution comprises between 0.05% and 3% by weight of collagen and preferably between 0.05%, 0.1%, 0.8%, 1%, 1.5%, 2%, 2.5% and 3% of collagen. Advantageously, the aqueous solution comprises 0.8% by weight of collagen. Said dissolution is usually carried out in water by mechanical stirring, preferably under reduced pressure.

The suspension or solution may also be heated at a temperature between 30° C. and 100° C. for 2 minutes to 20 minutes to partially or completely denature the collagen.

The methods according to the invention make it possible to obtain various collagen materials according to the form selected during molding or casting. The collagen material may thus notably take the form of a membrane, a matrix, a film, a thread, a gel, a tube or a sponge.

The casting or molding of an aqueous collagen solution is well known to the person skilled in the art and is described in the literature. The second step is thus the casting or molding of the collagen solution into molds, wherein the thickness varies according to the material desired and according to the surface of the mold.

Collagen membranes are two-dimensional materials that result from the drying in a flat mold of a homogeneous suspension or a collagen solution containing a proportion of fibers and fibrils. The collagen may or may not be cross-linked. The concentration of the dried suspension determines the thickness of the final material, which may range from a few microns to several hundred microns.

A collagen film is a two-dimensional material that results from the drying in a flat mold of a homogeneous collagen solution. The collagen may or may not be cross-linked. The concentration of the dried solution determines the thickness of the final material. Films and membranes may be folded to form sleeves which may be closed if need be by sutures or glue. The thickness may vary from a few microns to several hundred microns. A collagen tube is a hollow, three-dimensional cylindrical object whose walls may be a collagen film or membrane. Tubes may be obtained by molding around a mold or by extrusion. The collagen may or may not be cross-linked. Wall thickness is determined by the quantity of collagen deposited on the molds or used in the extrusion solution.

A collagen thread is a large assembly of collagen whose mechanical strength is sufficient to be part of the composition of a larger multi-stranded thread, a composite or non-composite textile or another collagen material.

A collagen sponge may be obtained by freeze-drying a collagen solution or suspension (or a mixture of the two). Before or after freeze-drying, the collagen may be cross-linked. Freeze-drying generally leads to three-dimensional materials or to powders.

In order to obtain a membrane or a film, the collagen solution may be deposited on a flat mold to obtain a two-dimensional material after drying the solution or suspension. The film or membrane may be obtained by evaporating the solvent.

Collagen tubes are obtained by depositing the solution or suspension on a cylindrical mold and drying or freeze-drying.

In order to obtain sponges, the solvent may be removed by freeze-drying and not by evaporating the solvent in liquid form.

It was previously known to use ammonia for coagulating and forming collagen but in general known methods involved the use of ammonia to coagulate a solution or a gel during extrusion, for example. Treating with ammonia was then very rapid and in baths. The method according to the invention rests on the diffusion rate of ammonia in the collagen solution, a rate that primarily depends on the concentration of this base on the surface of the solution. The collagen and the ammonia are left in contact for a period of time sufficient to enable coagulation of the collagen but also its fibrillation throughout the totality of the treated solution. This has led to the preparation of collagen materials with mechanical properties that are not obtained with the methods of the state of the art, in terms of tensile strength, elasticity and suture retention strength.

The third step is thus coagulating the collagen by treating it with ammonia for a period of time sufficient to enable both the coagulation and the fibrillation of the collagen. Typically, the ammonia treatment is carried out for a period of 4 hours, 8 hours, 12 hours, 24 hours, 36 hours or 48 hours. Preferably, the treatment period is greater than 24 hours or 36 hours.

The quantity of ammonia will be adjusted to increase the pH of the acidic-pH collagen gel to a pH of at least greater than 8. Indeed, cross-linking of the collagen begins when the collagen gel reaches a pH at least greater than 8. This long treatment enables a progressive increase in the pH of the collagen, which not only leads to its coagulation but also to its fibrillation. Depending on the length of the collagen fibers used, said fibrillation forms a meshwork which gives the materials both mechanical strength and elasticity.

In a preferred embodiment, ammonia gas is prepared from an ammonia solution from which it is released. A suitable quantity of ammonia gas is generally obtained from at least 30% ammonia solution at a temperature between 10° C. and 25° C. Preferably, this step is carried out in a hermetically sealed enclosure in such a way that the ammonia gas spreads inside the enclosure and comes into contact with the collagen solution, which is not in contact with the ammonia solution.

The collagen gel obtained is treated to remove excess ammonia and is either preserved as-is or in a dehydrated state. To that end, the gel may be placed in an enclosure equipped with a system to remove moisture and/or with an ammonia absorber. After removing excess ammonia, the membranes, films and tubes are obtained by dehydrating the gel under a stream of dry air, whereas sponges, 3-D matrices and tubes are obtained by freeze-drying the gel. Gels may be maintained in a hydrated state.

In said method for preparing collagen materials, the fibrillation process takes place in a highly viscous liquid medium. Said fibrillation occurs from the outside toward the inside of the solution and progresses with the increase in pH due to the diffusion of ammonia. It occurs when the pH reaches a value greater than 4 or 5. The advantage of the ammonia vapor method is that the material does not need to be immersed in neutralization solutions, which increases time savings, profitability and homogeneity.

When it is desired to increase the resorption time of a collagen medical device and also to strengthen its mechanical properties, the collagen material may be cross-linked. There are many collagen cross-linking methods well known to the person skilled in the art. They are grouped into two main categories: physical cross-linking such as, for example, thermal dehydration, and chemical cross-linking by adding or contacting with cross-linking agents. The most well-known collagen cross-linking agents are aldehyde agents, in particular formaldehyde and glutaraldehyde. Said cross-linking methods may of course be used on the collagen materials obtained above.

Thus, collagen and collagen materials may thus be cross-linked in order to increase their mechanical strength. Said cross-linking step is thus carried out after the last step d) of the method leading to the obtaining of the collagen material. It is carried out, for example, by immersing the collagen material in a bath comprising a cross-linking agent selected from formaldehyde, glutaraldehyde, oxidized glycogen and oxidized amylopectin.

Particularly advantageously, cross-linking may in contrast take place in a single step but in a sequential manner with coagulation and fibrillation of the collagen. In this case, an aldehyde agent that does not react with collagen at acidic pH is added to the starting collagen solution and then ammonia treatment is carried out to obtain a pH at least greater than 8.

The aldehyde cross-linking agent is preferably selected from polysaccharides, more particularly oxidized polysaccharides. Preferably, the aldehyde cross-linking agent is selected from oxidized glycogen and oxidized amylopectins. Cross-linking agents that may be used in the methods according to the present invention are, for example, oxidized starch, oxidized dextran and oxidized cellulose known to the person skilled in the art. Preferentially, the aldehyde cross-linking agent is oxidized glycogen.

The cross-linking agent is added in proportions ranging from 0.05, 0.1, 0.5, 1, 1.5, 2, 2.5, 3, 3.5, 4, 4.5 to 5 for the CHO ratio of the aldehyde cross-linking agent on the $NH_2$ of the collagen. The proportions of cross-linking agent may be adjusted by the person skilled in the art according to the cross-linking rate desired. The quantity of cross-linking agent to be added to the collagen solution may thus be determined using the general knowledge of the person skilled in the art.

Preferably, a concentrated (15%) aqueous solution of the selected oxidized polysaccharide is thus prepared. The oxidation rate and the quantity of cross-linking agent to be added are determined according to the resorption desired and the mechanical properties sought. It is then possible to add the cross-linking agent to the collagen in a perfectly controlled and reproducible quantity (unlike cross-linking by formaldehyde vapor, for example, or immersion in baths). Here, only the added cross-linking agent may react. The cross-linking solution is added to the collagen solution before casting or forming, i.e., at the end of homogenization under reduced pressure. The resulting medium is a homogeneous mixture of collagen and cross-linking agent, although bonds between the two have not been created since the mixture has not reached basic pH. The subsequent steps are identical to those of the fibrillation of collagen, wherein fibrillation and cross-linking are carried out successively and in that order.

The person skilled in the art will be able to adapt the quantity of ammonia and the exposure time to achieve the desired fibrillation and cross-linking.

This step of the method according to the invention is remarkable for several reasons. Cross-linking by aldehyde polysaccharides has already been described in the literature (Gagnieu C H and Forest P O, EP0862468). Said cross-linking may be carried out either by immersing the materials to be cross-linked in oxidized polysaccharide solution or by adding oxidized polysaccharide to the material and then immersing the dry product in a bath enabling the cross-linking reaction (increase in pH). In general, the change in pH is carried out by a buffer. Taking into account the well-known principle of cross-linking (Maillard reaction-→reaction of CHO groups of the cross-linking agent with $NH_2$ groups of the collagen), changing the pH using bases that themselves have amine residues is avoided. Thus, in the presence of ammonia, the theory predicts that the oxidized polysaccharide will react with the amine of ammonia and consequently will be inactivated. Cross-linking thus cannot take place.

In practice, it turns out that the presence of ammonia satisfactorily modifies the pH of the collagen gel to enable fibrillation but also cross-linking. In a completely surprising manner, cross-linking takes place at an effective rate because the Maillard reaction, which would have had to occur between the ammonia and the aldehydes of the cross-linking agent, thus inactivating the latter, is either absent, very weak, or not competitive with the cross-linking reaction between the aldehyde groups of the oxidized polysaccharide and the lysine amines of the collagen. This is demonstrated by the fact that materials cross-linked in this way are no longer soluble in acidic aqueous medium and have fewer degradations in contact with proteolytic enzymes than non-cross-linked materials, and by the fact that the mechanical properties of materials in hydrated form, and notably mechanical strength, are also improved in relation to non-cross-linked material.

The invention also relates to collagen material that may be obtained by the methods according to the invention. Preferably, the collagen material is cross-linked. Said collagen material may, for example, consist of a collagen membrane, a collagen thread, a collagen tube, a collagen sponge or a collagen gel.

The invention thus also relates to collagen films, threads and tubes that may be obtained by the methods according to the present invention. In one embodiment, the invention relates to collagen membranes that may be obtained by the methods according to the invention.

The methods according to the invention enable the preparation of dry membranes of variable thickness ranging from a few microns to a few hundred microns. The thickness generally used to ensure guided cicatrization (conservation of cleavage planes) or tissue substitution in urologic, gynecologic, cardiac, thoracic, vascular, articular, digestive, plastic, spinal, neurological, orthopedic, trauma, dental, oral and maxillofacial surgeries, for guided cicatrization of tissues (dura mater, gums, bones, nerves, tendons, ligaments, viscera, pericardium, peritoneum, conjunctive tissues in general, dermis, muscle, cartilage) is between 30 μm and 200 μm.

The invention thus relates to collagen membranes that may be obtained by the methods according to the invention that have a dry thickness between 30 μm and 200 μm. Preferably, said membranes are cross-linked.

Advantageously, said membranes consist of a non-porous collagen monolayer with a dry thickness between 50 μm and 150 μm.

In one embodiment, the object of the invention relates to collagen membranes that have a dry thickness between 80 μm and 120 μm, a density between 12 $mg/cm^2$ and 16 $mg/cm^2$, a swelling ratio less than 6, a suture retention strength greater than 1 N, a yield strength greater than 4 MPa and a percentage of enzymatic degradation by trypsin less than 35%.

In a preferred embodiment, the invention relates to the collagen membranes described above with a swelling ratio between 4 and 6, a suture retention strength between 1 N and 2.5 N, a yield strength between 4 Mpa and 7 MPa and a percentage of enzymatic degradation by trypsin between 20% and 35%.

Swelling ratio is measured as follows: 20 mg of material is immersed in 1× phosphate buffered saline, pH 7.4, for 60 minutes at 37° C. After the hour, excess water is removed with absorbent paper and the sample is weighed again. Swelling ratio is calculated by the ratio of the weight of the wet material to the weight of the dry material.

Measurements of mechanical stress (suture retention strength and yield strength) are measured on a moistened 5 mm-wide test tube using a tensile strength test bench. Regarding suture retention strength, a braided 3-0 polyamide suture thread is passed through the membrane and then the maximum force applied that breaks the suture is measured using a tensile strength test bench.

To determine enzymatic degradation by trypsin, fragments of material weighing between 10 mg and 20 mg are immersed in 3 ml of 1×PBS, pH 7.6, and 500 units of trypsin are added to the sample. After 48 hours of degradation, the digested samples are collected, dehydrated and weighed. The loss of weight in relation to the starting weight is then calculated.

The invention also relates to collagen membranes reinforced with a resorbable or non-resorbable textile. Said textile-reinforced membranes constitute a parietal reinforcement and are particularly suited to visceral and urogynecologic surgery or to a ligament patch to reinforce, extend or replace a ligament or a tendon.

Thus, another object of the invention relates to a composite material comprising, or consisting of, a textile covered on one side by a collagen material as described above.

It may notably be a textile bearing a collagen membrane according to the invention on one of its sides. Such prosthetic fabrics and methods for manufacturing same, for example, are described in U.S. Pat. No. 6,451,032.

The fabric-reinforced collagen membranes according to the invention may further be manufactured according to methods well known to the person skilled in the art.

In the context of the present invention, such a method may comprise the following steps:
preparing an aqueous solution of collagen in acid form,
adding an aldehyde cross-linking agent that is non-reactive at acidic pH,
molding or casting the aqueous collagen solution,
depositing the textile on the collagen,
coagulating and cross-linking the aqueous collagen solution by treating with ammonia,
removing the ammonia and obtaining the collagen material.

Membranes reinforced on one side with a textile obtained according to the method above are particularly suited for parietal surgery.

Alternatively, the method may comprise the following steps:
preparing an aqueous solution of collagen in acid form,
adding an aldehyde cross-linking agent that is non-reactive at acidic pH,
molding or casting the aqueous collagen solution,
including the textile in the collagen,
coagulating and cross-linking the aqueous collagen solution by treating with ammonia,
removing the ammonia and obtaining the collagen material.

Textiles thus comprising a membrane according to the invention on both sides are particularly suited for ligament surgery, for example.

Another object of the invention thus relates to a composite material comprising, indeed consisting of, a textile covered on two, notably on each, of its sides by a collagen material such as described above, wherein in particular the textile may be included in the collagen material.

Other methods for combining a collagen material according to the invention with a textile are known to the person skilled in the art.

The invention thus also relates to a collagen material according to the invention, notably a membrane, combined with a textile.

The methods according to the invention also lead to the preparation of tubes to ensure the guiding of organs in nerve, tendon, ligament and vascular surgery. Membranes for this indication may also be rolled and closed in sleeve form by suture and/or glue.

Lastly, the methods enable the preparation of porous or non-porous 3-D matrices greater than 200 μm in thickness which enable, among other things, inoculation of cells prior to or at the time of surgical implantation of the material for applications in regenerative medicine, and which enable suturable and elastic patches for cardiac applications, dura mater regeneration and guiding of soft and hard tissue to be obtained.

EXAMPLES

Example 1

Production of acidic fibrous Collagen of tendons

→Swelling of the Tendons

One kilogram of tendons from the feet of pigs is cleaned to remove muscle and aponeurotic tissue. They are immersed in 25 l of 0.3 M aqueous acetic acid solution for 10 days at 20° C. (±2° C.) under slow stirring.

→Grinding of the Tendons

Three liters of the suspension obtained is ground at 3000 rpm in a knife mill for 2 minutes. The medium is diluted with 2 l of water and then homogenized for 1 minute. The medium is filtered on a filter with a pore size of 200 μm and the filtrate is adjusted with 0.6 M NaCl to precipitate the collagen.

→Recovery of Collagen and Washes

The suspension is filtered or centrifuged to separate the precipitate from the supernatant. The precipitate is collected and washed in 10 l of 0.6 M NaCl under stirring for at least 1 hour; the precipitate is collected again by filtration on fabric or centrifugation. The washing step may be carried out the number of times desired according to the desired purity of the final collagen (ideally twice).

→Viral Inactivation and Washes

The precipitated and spun-dry collagen is dissolved to 1% in water for 16 hours under stirring. The concentration of the medium is brought to 1 M NaOH and the solution is stirred for 1 hour at 20° C. At the end of the inactivation step, the solution is neutralized with 6 M hydrochloric acid until the collagen precipitates. The collagen is recovered by filtration or centrifugation. The collagen may be washed again in 10 l of 0.6 M NaCl and then collected by filtration on fabric or by centrifugation. The washing step may be carried out the number of times desired according to the desired purity of the final collagen (ideally twice).

→Harvesting and Drying

At the end of the purification process, the precipitated collagen is spin-dried and then dried in acetone baths. The collagen is finally dried under a controlled stream of air to remove residual acetone and then stored at −20° C., for example.

Example 2

Characterization of a batch of acidic fibrous collagen of tendons 603 mg of acidic fibrous collagen of tendons with a water content of 17.05% is dispersed in 500 ml of demineralized water for 16 hours under magnetic stirring. A fabric with a pore size of 50 µm is placed on a 9 cm-diameter cylindrical support above a container. A volume of collagen solution is poured on the fabric in such a way as not to exceed 4 cm in height. A 7 cm-diameter blade is placed 2 mm from the fabric and rotated at 80 rpm; the collagen solution gradually flows through the fabric. When the volume contained in the upper chamber decreases no further, the system is reloaded in such a way as to never exceed 4 cm in height. Said operations are carried out until the prepared solution is exhausted. Upon equilibration of the system, the retentate is washed with 3×50 ml of 0.05 M acetic acid with the same system, while respecting pressure differentials. The upper fraction is collected.

The lower fraction is recovered and the analysis is continued in the same way on a fabric with a pore size of 5 µm. Retentate as well as filtrate are collected.

The three fractions, i.e., retentate from the 50 µm filtration and retentate and filtrate from the 5 µm filtration, are brought to 0.6 M NaCl and the collagen is recovered by centrifugation and then dried in two baths of 70% acetone and then baths of 100% acetone. Excess acetone is removed by drying under a stream of air. The fractions are weighed and compared to the total weight collected. Analysis shows that 6.5% of the fibers are retained on a 50 µm filter, 27% of the fibers crossed a 5 µm filter and thus 66.5% are between 5 µm and 50 µm.

Example 3

Preparation of a cross-linked collagen film/membrane #1

800 mg of acidic fibrous collagen of tendons is suspended under mechanical stirring in 100 ml of water for 16 hours. The viscous suspension is poured into a mold at a density of 4 mg of collagen/cm$^2$. The mold containing the collagen solution is placed in a 3 l hermetically sealed enclosure containing 2 ml of 30% ammonia for 24 hours at 20° C. The gel is placed in an enclosure for removing excess ammonia with an ammonia and moisture absorber in order to obtain a film roughly 40 µm in thickness. The film may be used as-is or cross-linked by immersion in a bath of formaldehyde, glutaraldehyde, oxidized glycogen or oxidized amylopectin of various concentrations for periods ranging between 2 minutes and 24 hours. Cross-linking agents are inactivated by immersing the film in a 0.1 M glycine solution, pH 8, for 2 hours. The film is then dried again.

For example, the film obtained after the first drying is immersed for 1 hour in a 0.1% formaldehyde bath, pH 8, and then rinsed in a 0.1 M glycine bath, pH 8, for 2 hours. After a rinsing with water, the film is dried again.

Example 4

Preparation of a cross-linked collagen membrane #2

In order to obtain a membrane containing 10 mg of collagen/cm$^2$, 100 g of collagen is suspended in 12.5 l of water under mechanical stirring for 16 hours. At the same time, 2.5 g of oxidized glycogen dissolved to 15% in pH 7.7 phosphate buffer is prepared and added to the suspension at the end of the 16 hours. After homogenization, the solution is poured into 1 m$^2$ molds (or equivalent). The molds containing the collagen solution are placed in a roughly 300 l hermetically sealed enclosure containing 160 ml of 32% ammonia distributed homogeneously for 48 hours at 20° C. At the end of the fibrillation and cross-linking phase, the gels are placed in an enclosure for removing excess ammonia with an ammonia and moisture absorber in order to obtain a membrane roughly 100 µm in thickness.

Example 5

Measurement of the swelling ratio of a membrane prepared in example 4

Three samples of 20.5 mg, 22 mg and 20 mg of material are weighed precisely and immersed in 3 ml of 1×PBS, pH 7.4, for 1 hour at 37° C. At the end of the hour, excess water from each sample is removed and the samples are weighed again. The results are as follows:

|  | Sample weight | Weight after swelling | Swelling ratio |
| --- | --- | --- | --- |
| Sample 1 | 20.5 | 110 | 5.5 |
| Sample 2 | 22 | 127.6 | 5.8 |
| Sample 3 | 20 | 114 | 5.7 |
| Average |  |  | 5.66 |

Example 6

Sponge of acidic fibrous collagen cross-linked by oxidized amylopectins

An aqueous solution of acidic fibrous collagen is obtained by mixing 0.8 g of acidic fibrous collagen in 100 ml of water. The medium is stirred for 16 hours at 20° C. 28 mg of amylopectin containing 1.4 moles of aldehydes/mole of saccharides is heated at 75° C. in 1 ml of 0.1 M phosphate buffer, pH 7.7, until complete dissolution. After cooling to 20° C., said solution is poured under stirring into the 0.8% collagen solution. The homogeneous medium is poured into a mold to a height of 5 mm and transferred to a hermetically sealed enclosure of roughly 3 l in volume containing 3 ml of 28% ammonia for 16 hours. The device containing the gel is then placed in a hermetically sealed enclosure containing an ammonia absorber until all the ammonia in the enclosure is removed. The collagen gel is then frozen and then freeze-dried to yield a sponge of cross-linked atelocollagen.

Example 7

Measurement of cross-linking homogeneity

A gel roughly 1 cm in thickness was prepared by the method described in example 4 up to the cross-linking step.

At the end of said cross-linking step, the gel was unmolded, cut into two, approximately in the middle, in the horizontal direction, and the two sections were dried separately.

An "external" and an "internal" sample of material (roughly 10 mg each) are taken from areas corresponding to the external portion and the internal portion of the gel, respectively.

Cross-linking rate is determined by an assay of amines remaining free in the collagen by TNBS (2,4,6-trinitrobenzenesulfonic acid). Said TNBS reagent specifically reacts with amines of lysine residues and free terminal amino acids.

The internal and external samples are taken and incubated in a water/propanol solution (1 ml) at 60° C. for 1 hour. 500 µl of 8% bicarbonate and 1 ml of TNBS diluted to 1/120 are added. The reaction takes place for 3 hours at 40° C.

After cooling, 200 µl of 6 N HCl is added to quench the reaction. Excess TNBS is extracted with 5 ml of ethyl acetate. Acid hydrolysis (3 ml of 6 N HCl for 1.25 hours) releases all the amino acids. N-TNBS terminal amino acids are extracted in the same manner as excess TNBS.

After adequate dilution, absorbance of the aqueous phase is measured at 345 nm. The molar extinction coefficient of the complex at 345 nm, measured according to the protocol described by Kakade et al., is $1.46 \cdot 10^{-4}$ $M^{-1} \cdot cm^{-1}$, which makes it possible to calculate the quantity of lysines remaining free in the membrane. The result is expressed in µmol of free lysines per mg of membrane.

For a membrane cross-linked with oxidized glycogen in a ratio of 0.4 CHO of oxidized glycogen for 1 $NH_2$, the results are as follows:

|  | µmol of free lysine/mg of membrane |
| --- | --- |
| External sample | 0.161 |
| Internal sample | 0.150 |

The difference in cross-linking is thus 3.5%, which is ((0.161-0.150)/(0.161+0.150)×100). The cross-linking rates of the external portion and the internal portion are thus roughly the same. Cross-linking is thus quite homogeneous throughout the thickness of the material.

Example 8

Measurement of cross-linking

A so-called "cross-linked" membrane was prepared according to the method described in example 4, including the step of adding ammonia.

A so-called "non-cross-linked" membrane was prepared according to the method described in example 4, wherein the step of adding ammonia is omitted.

Cross-linking may be measured using differential scanning calorimetry (DSC). Said method measures the differences in the transfer of heat between a sample to be analyzed and a reference.

DSC is used to detect phase transitions:
glass transition temperature ($T_g$)
fusion or denaturation temperatures
reaction enthalpies (to determine the cross-linking rates of polymers).

The analyses are carried out under a stream of inert gas (nitrogen or argon, for example) to avoid any reaction of the material studied with the atmosphere of the furnace.

With regard to collagen, cross-linking increases denaturation temperature. To demonstrate that incubating the collagen solution containing the cross-linking agent in ammonia vapors leads to the formation of stable chemical cross-linking bonds between the collagen and the cross-linking agent, the DSC profile of a cross-linked membrane and a non-cross-linked membrane were determined.

|  | Denaturation temperature (° C.) |
| --- | --- |
| Cross-linked membrane | 49.62 |
| Non-cross-linked membrane | 42.37 |

The denaturation temperature of the cross-linked membrane is thus clearly higher than that of the non-cross-linked membrane. The reaction between the aldehyde cross-linking agent and the collagen thus clearly takes place during the incubation of the solutions in ammonia vapors.

REFERENCES

Forest P O, Karoum R, Gagnieu C H. Influence of gradual introduction of hydrophobic groups (stearic acid) in denatured atelocollagen on fibroblasts behavior in vitro, J Biomed Mater Res A. 2007 Mar. 1; 80(3): 758-67.

Gagnieu C H, Forest P O. In vivo biodegradability and biocompatibility of porcine type I atelocollagen newly crosslinked by oxidized glycogen, Biomed Mater Eng. 2007; 17(1): 9-18).

Rousseau C F and Gagnieu C H. In vitro cytocompatibility of porcine type I atelocollagen crosslinked by oxidized glycogen. Biomaterials, 2002. 23(6): p. 1503-10.

Kakade M L, Liener I E. Determination of available lysine in proteins. Anal Biochem, 1969; 27(2): 273-280

PATENT REFERENCES

WO2007/147739
FR2810889
FR2877669
EP0862468
U.S. Pat. No. 4,931,546

The invention claimed is:

1. A collagen material comprising one of a collagen membrane, a collagen film, a collagen thread, a collagen tube, a collagen sponge or a collagen gel, wherein said collagen material comprises a density between 12 $mg/cm^2$ and 16 $mg/cm^2$, a swelling ratio less than 6, a suture retention strength greater than 1N, a yield strength greater than 4 MPa and a percentage of enzymatic degradation by trypsin less than 35%.

2. The collagen material of claim 1, wherein said collagen material comprises homogenous cross-linking with a difference between crosslinking on the outside surface and cross-linking inside the material of less than or equal to 25%.

3. The collagen material of claim 1, wherein said collagen material has an increase in denaturation temperature greater than or equal to 3° C. in relation to non-cross-linked collagen material.

4. The collagen material of claim 1, wherein said collagen material has an increase in denaturation temperature in relation to non-cross-linked material of at least 5%.

5. The collagen material of claim 1, wherein said collagen material is a collagen membrane having a length and width greater than 5 cm.

6. A collagen membrane comprising a dry thickness between 30 µm and 200 µm, a density between 12 $mg/cm^2$ and 16 $mg/cm^2$, a swelling ratio less than 6, a suture retention strength greater than 1N, a yield strength greater than 4 MPa and a percentage of enzymatic degradation by trypsin less than 35%.

7. The collagen membrane of claim 6, wherein said collagen membrane consists of a non-porous collagen monolayer with a dry thickness between 50 μm and 150 μm.

8. The collagen membrane of claim 6, wherein said collagen membrane comprises a dry thickness between 80 μm and 120 μm.

9. The collagen membrane of claim 6, wherein said collagen membrane comprises a swelling ratio between 4 and 6, a suture retention strength between 1N and 2.5 N, a yield strength between 4 MPa and 7 MPa and a percentage of enzymatic degradation by trypsin between 20% and 35%.

10. A composite material comprising a textile covered on one of its sides by a collagen material comprising a density between 12 mg/cm$^2$ and 16 mg/cm$^2$, a swelling ratio less than 6, a suture retention strength greater than 1N, a yield strength greater than 4 MPa and a percentage of enzymatic degradation by trypsin less than 35%.

11. A composite material comprising a textile covered on each of its sides by a collagen material comprising a density between 12 mg/cm$^2$ and 16 mg/cm$^2$, a swelling ratio less than 6, a suture retention strength greater than 1N, a yield strength greater than 4 MPa and a percentage of enzymatic degradation by trypsin less than 35%.

12. The composite material of claim 11, wherein said textile is embedded in said collagen material such that both sides of the textile is covered by said collagen material.

13. The collagen material of claim 1, wherein said collagen sponge is in the form of a powder.

* * * * *